United States Patent [19]

Manzoni et al.

[11] Patent Number: 5,227,305
[45] Date of Patent: Jul. 13, 1993

[54] BUFFER SOLUTION SYSTEMS FOR STANDARDIZING PH ANALYZERS AND ELECTROLYTES

[75] Inventors: Angelo Manzoni, Brugherio; Mario Belluati, Brescia, both of Italy

[73] Assignee: Instrumentation Laboratory SpA, Milano, Italy

[21] Appl. No.: 840,637

[22] Filed: Feb. 21, 1992

Related U.S. Application Data

[63] Continuation of Ser. No. 714,997, Jun. 11, 1991, abandoned, which is a continuation of Ser. No. 350,950, May 11, 1989, abandoned.

[30] Foreign Application Priority Data

May 13, 1988 [IT] Italy ................ 20560 A/88

[51] Int. Cl.$^5$ ............................................. G01N 31/00
[52] U.S. Cl. ........................................... 436/19; 436/8; 436/17; 436/18
[58] Field of Search ...................... 436/8–19; 252/408.1

[56] References Cited

U.S. PATENT DOCUMENTS

| | | | |
|---|---|---|---|
| 4,279,775 | 7/1981 | Louderback et al. | 436/18 |
| 4,363,633 | 12/1982 | Christiansen | 436/19 |
| 4,686,479 | 8/1987 | Young et al. | 324/436 |
| 4,786,394 | 11/1988 | Enzer et al. | 204/401 |
| 4,806,486 | 2/1989 | Sprokholt et al. | 436/19 |
| 4,843,013 | 6/1989 | Chiang | 436/18 |
| 5,070,023 | 12/1991 | Calabrese | 436/8 |

FOREIGN PATENT DOCUMENTS 2456628 6/1975 Fed. Rep. of Germany ........ 436/18
8706343 10/1987 PCT Int'l Appl. .

OTHER PUBLICATIONS

A. Sibbald et al., "Online patient monitoring system for the simultaneous analysis ...", Medical & Biol. Eng. & Comp., vol. 23, No. 4, pp. 329–338 (Jul. 1985).

*Primary Examiner*—James C. Housel
*Assistant Examiner*—N. Bhat
*Attorney, Agent, or Firm*—Testa, Hurwitz & Thibeault

[57] ABSTRACT

A formulation of combined-composition electrolyte and pH buffers for use as standardization solutions in analyzers for clinical chemistry which simultaneously use more than one ion-selective electrode plus more than one standard solution. Each ion is present in the standard solution in stoichiometric quantity such as to compensate the effect due to the incomplete dissociation of the salt used, and to obtain an activity coefficient and liquid junction potential such as to reduce the error generated by the use of standardization solutions which do not take account of these quantities. Buffer solutions are described having a pH within the range of 6–8 and an electrolyte compositions ($Na^+$, $K^+$, $Ca^+$ and $Cl^-$) which reflect the composition of the biological liquid to be analyzed, namely whole blood, plasma or serum, in equilibrium with different partial pressures of oxygen and $CO_2$.

15 Claims, No Drawings

BUFFER SOLUTION SYSTEMS FOR STANDARDIZING PH ANALYZERS AND ELECTROLYTES

This is a continuation of copending application Ser. No. 07/714,997 filed on Jun. 11, 1991, now abandoned, which is a continuation of Ser. No. 350,950 filed May, 11, 1989, now abandoned.

This invention relates to analytical systems for clinical chemistry and more specifically to standardization, standard and/or control solutions used therein for the specific determination of ions (activity or concentration) by direct potentiometry using ion-selective electrodes.

The continuous development of electroactive components for the formulation of ion-selective electrodes of various types enables a vast number of cations and anions to be determined. At present there are at least 30 ion species (anions and cations) which can be determined selectively by direct potentiometry using different types of ion-selective electrodes (Daniel Ammann, Ion-selective microelectrodes, principles, design and application —Springer Verlag, Berlin, Heidelberg, 1986).

Altough glass membrane electrodes are still widely used in analytical chemistry for determining hydrogen ion and sodium ion activity, neutral carrier-based electrodes are gradually assuming significant strategic importance in the determination of alkali and alkaline-earth metals.

In particular, analytical systems for electrolyte determination in the blood, serum and plasma based on direct potentiometry use ion-selective electrodes for sodium, potassium, calcium, lithium and chloride together with the already established pH sensor.

Blood is a complicated biological liquid containing various components of fundamental importance in physiological activity.

An analytical technique which directly indicates the concentration of a substrate in the blood aqueous phase containing both electrolytes and other species such as proteins and lipids either dissolved or present in colloidal form provides fundamental clinical information particularly under conditions of blood abnormality. In this respect, dilution would result in loss of the important information which derives from direct measurement of the intensive properties (concentration) of the system under test.

The indirect method is in fact dependent on the volume of diluting solution, the aqueous part of which will depend on the concentration and types of proteins or lipids present.

The actual ion-selective electrode is an electrochemical half-cell consisting of an internal reference system and the specific membrane, the formulation and function of which depend on the characteristics of the ion to be measured.

The remaining half-cell is an external reference electrode in contact with a standard electrolyte, such as Ag/AgCl in saturated KCl.

The membranes can be of different type according to the ion to be determined.

The potential of the electrochemical cell (electromotive force-EMF, potential difference at zero current) arises when the membrane electrode and reference electrode are both in contact with the solution to be measured.

The electromotive force is the sum of a series of local potential differences generated at the solid-solid, solid-liquid and liquid-liquid interface.

Ideally, the potential difference generated between the membrane and solution to be measured depends on the activity of the types of ion in the sample.

If all other potential differences are assumed constant, the electromotive force of the cell is described by the Nernst equation.

In practice however, the electrochemical system never exibits this ideal behaviour.

Deviations from the Nernst equation sometimes become significant and it is therefore necessary to take account of additional contributions to the electromotive force by interfering ions.

The Nicolsky-Eisenman equation, which is an extension of the Nerst equation, provide a satisfactory semiempirical approach to describing the system, namely:

$$EMF = E_o + S \log \left( a_i + \sum_{i}^{n} j\, K_{ij}(a_j)\, z_i/z_j \right)$$

where $k_{ij}$ is the selectivity factor.

Again, $E_o = E^o{}_i + E_R + E_D$ where:

$E^o{}_i$ is a constant potential difference including the surrounding potential differences which arise between the filling solution and the membrane, $E_R$ is a constant potential difference depending on the potential difference between the metal conductor and the filling solution of the indicator electrode (ion-selective) and the potential difference between the metal conductor and the standard electrolyte in the reference electrode; $E_R$ is independent of variations in the composition of the sample, $E_D$ is the interliquid potential difference generated between the standard electrolyte and the solution to be examined.

The sum of $E^o{}_i$ and $E_R$ contains all the contributions which remain independent of the sample composition, $E_D$ is variable and depends on the sample, it being generated at the interface between the standard electrolyte (salt bridge) and the solution to be measured, and can sometimes vary significantly.

Obviously, $E_D$ is added to the potential difference at the membrane, and this contribution must be minimized by suitable choice of the standard electrolyte (the reference junction most commonly used is saturated KCl—4,2M at 25° C., or 3M).

Again, the electromotive force of an electrochemical cell with an ion-selective electrode and liquid junction depend on the logarithm of the ion activity, which itself depends on the ion concentration in terms of the stoichiometric quantity of the substance. For ionic strenghts >0.01M, such as found in biological matrices, the concentration cannot be a substitute for activity.

The activity coefficients which relate activity to concentration determined by solutions in mixed electrolytes containing for example physiologically important ions and proteins would much more adequately describe the conditions in biological liquids.

However this approach unfortunately encounters considerable difficulties in that the instrument which determines the value of the activity coefficient by direct potentiometry would have to be the ion-selective electrodes themselves.

Activity scales for pH measurement in physiological solutions of hydrogen ion activity have been successfully introduced (R. G. Bates, C. Vega: Standard for pH measurement in isotonic saline media of ionic strength I=0.16; Analytical Chemistry vol. 50, No. 9, August 1978).

The subject of activity coefficients is closely associated with calibration problems and the experimental arrangement of the measuring cell.

According to the present invention it is proposed to improve standardization solutions (calibration and control) for analyzers using direct potentiometry with ion-selective electrodes, by providing them with compensation obtained by adding supporting or active salts or electrolytes, which approximate the value of the activity coefficient and reduce the differences originating from the interliquid potential between the reference standard and the sample.

Expressed in terms of correction factor, the effect can be indicated schematically by the following ratios:

$$\frac{\gamma_f(\text{sample solution})}{\gamma_f(\text{standard solution})} : \text{for the activity coefficient and}$$

$$\frac{E_f(\text{sample solution})}{E_f(\text{standard solution})} : \text{for interliquid potential}$$

Accurate calibrations for pathological fluids are obtained with so-called compensated standardizations in which the aforesaid ratios approximate to 1.

In practice, the compensation is obtained with salts which act on the interliquid potential and on the activity coefficient which, in the contingency herein described, is obtained by adding NaCl, KCl and CaCl$_2$ in suitable stoichiometric quantity to obtain best compensation for each ion measured, and obtain the data according to the reference system (Na+ and K+ by flame photometry and Ca by atomic absorption).

The conventional "buffer pair" (pH 7.384 and pH 6.840 at 37° C.) for standardizing current pH/ISE analyzers, obtained by suitably mixing phosphates of alkali metals in accordance with the NBS formulation, is unsuitable for the simultaneous standardization of sodium, potassium, calcium and chloride for reasons discussed below in connection with table 1 and 2.

The present invention provides a standardization system for use with a clinical chemistry analyzer having ion selective electrode means for simultaneous or discrete determination in whole blood, plasma or serum of pH and of Na, K, Cl and Ca ions. The standardization system comprises two buffer solutions. The second buffer solution has non-zero values of pH and of Na, K, Cl and Ca ions different from the non-zero values of pH and of Na, K, Cl and Ca ions of the first buffer solution. The first and second buffer solutions each contain a Good's Buffer in addition to defined amounts of sodium, potassium, chloride and calcium ions. Advantageously the first buffer solution contains the buffer pair HEPES/NaHEPES at a concentration of 40 to 60 mmol/liter and the second buffer solution contains the buffer pair MOPS/NaMOPS at the concentration of 40 to 60 mmol/liter.

The invention proposes the formulation of combined-composition buffers for electrolytes and pH, suitable for simultaneous standardization of analyzers using the potentiometric method with ion-selective electrodes.

The chosen criteria for formulating these standardization solution according to the invention were:

buffer solutions having a pH in the range 6-8 at 37° C.;

solutions having an ionic strength as similar as possible to that of whole blood;

solutions in which the variation of the ions concerned reflected that in the blood;

solutions which as far as possible did not contain ions normally absent from the blood;

solutions prepared with substances having a high state of purity and easily available commercially;

solutions in which an ionic concentration difference gives a significant difference in terms of $\Delta E$ ($\Delta E > 8$ mV), while still reflecting the ion variation in the blood.

Preferred standardization system are ones meeting all of these criteria, but the standardization systems are suitable in accordance with the invention even if some of the criteria are not met entirely.

The literature data were taken as the starting point for their formulation (R. G. Bates, C. Vega, cited article).

Once prepared, the buffer solutions were subjected to a series of tests regarding two aspects of specific interest, namely 1) pH, and 2) concentration of electrolytes (Na+, K+, etc.).

The pH of the buffer solutions was measured at 37° C. with a pH glass electrode as the indicator electrode and a calomel in saturated KCl reference electrode with an open junction.

The calibration was done with buffers obtained from NBS standard reference Products, namely pH 6.840 at 37° C., 0.025 molar in KH$_2$PO$_4$ and NA$_2$HPO$_4$; pH 7.384 at 37° C., 0.008695 molar KH$_2$PO$_4$ and 0.03043 molar NA$_2$HPO$_4$.

The sodium and potassium composition was checked by flame emission photometry and calcium by atomic absorption.

By this method a check was obtained on the total quantity of sodium, potassium and calcium for comparison with the result obtained at the electrodes (ISE) both at 37° C. and 25° C.

The electrodes had previously been standardized with pure NaCl, KCl and CaCl$_2$ solutions. Table 1 shows an example of the results obtained for pH 7,4 at 37.C, IS 0,16 with phosphate buffer to NBS formulation:

TABLE 1

|  | Flame photometry moles/l | ISE 25° C. moles/l | ISE 37° C. moles/l |
| --- | --- | --- | --- |
| Na+ | 154 | 135 | 140 |
| K+ | 5.4 | 4.4 | 4.8 |

Table 2 shows an example of the results obtained for pH 6,8 at 37° C., IS 0,16 M with phosphate buffer to NBS formulation:

TABLE 2

|  | Flame photometry moles/l | ISE 25° C. moles/l | ISE 37° C. moles/l |
| --- | --- | --- | --- |
| Na+ | 100 | 85 | 90 |
| K+ | 8 | 6.1 | 6.3 |

The results show that calibrating the ion-selective electrodes for sodium and potassium with alkaline phosphate buffers of ionic strength 0.16 leads to a different measurement if compared with non-buffered solutions and gives results less than those of flame photometry or in any event less than the stoichiometric quantity present in the solution.

TABLE 3

| pH | Δ% ISE/FF 25° C. | | Δ% ISE/FF 37° C. | |
|---|---|---|---|---|
| | Na+ | K+ | Na+ | K+ |
| 7.4 | 88 | 82 | 91 | 88 |
| 6.8 | 85 | 76 | 90 | 79 |

Table 3 shows that this effect can be partly attributed to the contribution of the liquid junction potential originated by the buffer obtained by the phosphate species. In this respect, the differences indicate that the sodium ions and potassium ions undergo ionic association phenomena with the phosphate buffer.

The extent of this effect was in all cases such as to make it clearly desirable to obtain a buffer pair which behaved towards the electrolytes as a "primary" standardization solution, with behaviour similar to an aqueous NaCl, KCl and CaCl₂ solution the pH of which is however adequate for the standardization of an analytical system for determining pH, sodium, potassium, calcium and chloride in the blood and undiluted serum.

For this reason, according to the invention attention was fixed on some derivatives in the form of ethane and propane sulphonic acid (i.e. Good's Buffer: TES, HEPES, MOPS and MOPSO) with pH values such as to allow buffers to be prepared within the stated pH range (6–8)

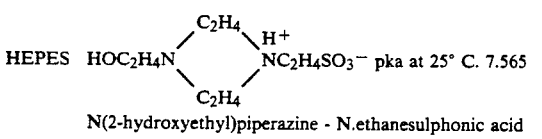

N(2-hydroxyethyl)piperazine - N.ethanesulphonic acid

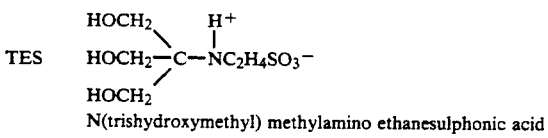

N(trishydroxymethyl) methylamino ethanesulphonic acid

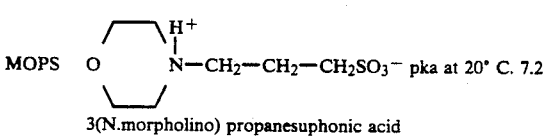

3(N.morpholino) propanesuphonic acid

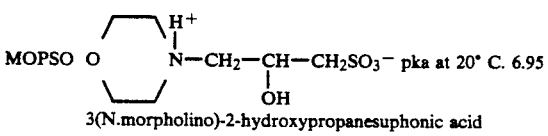

3(N.morpholino)-2-hydroxypropanesuphonic acid

In attaining the objects of the invention it was considered an essential preliminary to solve the problem of compensation of the aspect related to the incomplete dissociation.

The analysis of this condition was extended by using as reference a buffer system based on the pair trishydroxymethylamino-methane (Tris)—Tris HCl, pH 7.5 at 25° C., identified as among those which during experimental work had shown little binding capacity towards either sodium, potassium or calcium.

As an example, Table 4 shows the variation in the electromotive force of the Ca electrode against SCE cell in solutions of the given concentration.

TABLE 4

Data on the potential of the calcium electrode in the respective solutions at 25° C. and 37° C.

| | Sol. 1 | Sol. 2 | Sol. 3 |
|---|---|---|---|
| 25° C. | +42.3 mV | +42.5 mV | +42.6 mV |
| 37° C. | +42.8 mV | +42.8 mV | +42.8 mV |

| Sol. 1 | 1 mM Tris/Tris HCl, 160 mM NaCl, 1 mM CaCl₂ | pH 7.2 at 37° C. (7.5 at 25° C.) |
| Sol. 2 | 10 mM Tris/Tris HCl, 152 mM NaCl, 1 mM CaCl₂ | |
| Sol. 3 | 100 mM Tris/Tris HCl, 80 mM NaCl, 1 mM CaCl₂ | |

Table 5 shows the sodium and potassium variation for ISE against SCE at various Tris/Tris HCl concentrations.

TABLE 5

Data on electrode potentials against SCE for NA+ and K+ at temperature of 5° C. and 37° C.

| 1 | 50 | 100 | Conc. in Tris/Tris HCl m.moles/l |
|---|---|---|---|
| Sodium electrode | | | |
| −11.1 | −10.9 | −10.9 | Electrode pot. (mV) at 25° C. |
| −13.3 | −12.88 | −12.7 | Electrode pot. (mV) at 37° C. |
| Potassium electrode | | | |
| +56.7 | +56.9 | +56.9 | Electrode pot. (mV) at 25° C. |
| +47.7 | +47.6 | +47.6 | Electrode pot. (mV) at 37° C. |
| Sol. 1 | 1 mM Tris/Tris HCl 140 mM NaCl 5 mM KCl | | pH 7.2 at 37° C. |
| Sol. 2 | 50 mM Tris/Tris HCl 140 mM NaCl 5 mM KCl | | |
| Sol. 3 | 100 mM Tris/Tris HCl 140 mM NaCl 5 mM KCl | | |

Using this preliminary analysis an investigation was made of the buffer pair (among those reported) which gave the best buffer effect and the least complexing (binding) effect towards sodium, potassium and calcium.

The standardization system used for sodium and potassium involved the use of a Tris/Tris HCl 1 mM buffer of pH 7.5 at 25° C., of 140 mM Na+ and 5 mM K+, and of 100 mM Na+ and 3mM K+.

Table 6 shows the effect of the concentration of the HEPES/NaHEPES buffer pair (pH 7.4 at 37° C.) on the sodium and potassium determination.

TABLE 6

Data on concentrations in mmoles of Na and K for various HEPES/NaHEPES concentrations at 25° C. and 37° C.

| Sol A | Sol B | Sol C | Sol D | Sol E | HEPES/ NaHEPES conc. |
|---|---|---|---|---|---|
| 1 | 10 | 25 | 50 | 100 | |
| a) Sodium | | | | | |
| 140 | 140 | 138 | 137 | 133 | Na conc. mmoles/l at 25° C. |
| 139 | 138 | 136 | 135 | 130 | Na conc. mmoles/l at 37° C. |
| −0.7 | −1.4 | −3 | −3.6 | −7.1 | ΔC% against ref. 37° C. |
| 1 | 10 | 25 | 50 | 100 | |
| b) Potassium | | | | | |
| 5 | 5 | 5 | 4.9 | 4.8 | K conc. mmoles/l at 25° C. |

TABLE 6-continued

Data on concentrations in mmoles of Na and K for various HEPES/NaHEPES concentrations at 25° C. and 37° C.

| Sol A | Sol B | Sol C | Sol D | Sol E | HEPES/NaHEPES conc. |
|---|---|---|---|---|---|
| 4.9 | 4.9 | 4.9 | 4.8 | 4.6 | K conc. mmoles/l at 37° C. |
| −2 | −2 | −2 | −4 | −8 | ΔC% against ref. 37° C. | c) Calcium

| | | | | | |
|---|---|---|---|---|---|
| | 0.98 | 0.96 | 0.96 | 0.87 | $Ca^{++}$ conc. mmoles/l at 25° C. |
| | 1 | 0.95 | 0.97 | 0.89 | $Ca^{++}$ conc. mmoles/l at 37° C. |
| | | 5 | 3 | 11 | ΔC% against ref. 37° C. |

For up to 50 mM HEPES/NaHEPES, preferably for 40 to 60 mM concentration of this buffer pair, the effect due to ion complexing by the buffer can be excluded and the differences be attributed to the interliquid potential established at the saturated KCl junction.

To confirm this assumption the calcium concentration at the calcium electrode was read in a series of solutions of constant sodium ion concentration using the sodium electrode as the reference electrode.

The calibration was done with 1 and 3 mM $Ca^{++}$ in Tris/Tris HCl 0.01 M buffer, pH 7.5 at 25° C. in 140 mM $Na^{+}$.

The results are shown in Table 7. The measurement solutions differ in HEPES/NaHEPES concentration.

TABLE 7

| HEPES/NaHEPES mM | 10 | 25 | 50 | 100 |
|---|---|---|---|---|
| Calcium observed at 25° C. against $Na^{+}$ electrode as reference | 1.02 | 1.01 | 1.00 | 1.00 |
| Calcium observed at 25° C. against SCE | 1.00 | 0.95 | 0.92 | 0.90 |

These experimental results obtained by keeping the ionic strength constant confirm that the contribution provided by the interliquid potential (against ref. SCE) is determining.

The greater accuracy difference (about double concentration) deriving from it for calcium compared with sodium and potassium is attributable to the double charge of the first ion compared with the others.

Table 8 shows the results of a similar experiment conducted for sodium and potassium in MOPS/NaMOPS buffer at different concentrations.

TABLE 8

Data on concentrations in mmoles of Na and K for various MOPS/NaMOPS concentrations at 25° C. and 37° C.

| Sol 1 1 | Sol 2 10 | Sol 3 25 | Sol 4 50 | Sol 5 100 | MOPS/NaMOPS conc. |
|---|---|---|---|---|---|
| a) Sodium | | | | | |
| 101 | 99 | 98 | 99 | 92 | Na conc. mmoles/l at 25° C. |
| 100 | 99 | 98 | 99 | 93 | Na conc. mmoles/l at 37° C. |
| b) Potassium | | | | | |
| 3 | 3.2 | 2.9 | 3 | 2.9 | K conc. mmoles/l at 25° C. |
| 3. | 3.05 | 2.9 | 2.9 | 2.85 | K conc. mmoles/l at 37° C. |

The situation is not as simple as in the case of HEPES/NaHEPES.

Again in this case, considering a concentration of 50 mmoles/l of MOPS/NaMOPS, preferably for 40 to 60 mM concentration of this buffer, the effect on sodium and potassium can be considered comparable with that expected.

Both for MOPS/NaMOPS and HEPES/NaHEPES, according to the invention experiments were carried out on the preparations having a concentration of 50 mmoles/l by effecting the compensations which the experimental results had shown necessary for the electrolytes in terms of ionic strength and liquid junction.

| CORRECTION TO BE MADE IN TERMS OF STOICHIOMETRIC CONCENTRATION COMPARED WITH THAT EXPECTED | | | |
|---|---|---|---|
| | $Na^{+}$ | $K^{+}$ | $Ca^{++}$ |
| HEPES/NaHEPES | | | |
| 50 mmoles/l | +4% | +4% | +8% |
| MOPS/NaMOPS | | | |
| 50 mmoles/l | +1% | +1% | +2% |

The next experiment was to obtain for the two described buffer solutions the required pH value, namely pH 7.384 (HEPES/NaHEPES) and pH 6.840 (MOPS/NaMOPS) at 37° C., by suitably modifying their proportions while maintaining their total molarity (50 mmoles/litre) constant.

The hydrogen ion activity was determined on a system with a glass electrode and open junction using calomel in saturated KCl at 37° C. Standardization was obtained with phosphate buffers of NBS formulation (7.384 and 6.840 at 37° C.).

The buffer stoichiometric compositions are given in Table 9.

| A) HEPES/NaHEPES buffer | | |
|---|---|---|
| | mmoles/l | pH 7.384 at 37° C. |
| NaHEPES | 27.5 | |
| HEPES | 22.36 | |
| NaCl | 119 | |
| KCl | 5.2 | |
| $CaCl_2$ | 1.8 | |
| B) MOPS/NaMOPS buffer | | |
| | moles/l | pH 6.840 at 37° C. |
| NaMOPS | 23.25 | |
| MOPS | 28.76 | |
| NaCl | 77.75 | |
| KCl | 2.02 | |
| $CaCl_2$ | 3.06 | |

+ 20 mg/l of phenylmercuric nitrate ($C_6H_5HgOHC_6H_5HgHO_3$)

Table 10 illustrated one example of the control method used to verify the behaviour of the solutions according to the invention.

TABLE 10

| | pH meter 37° C. open liquid junction | pH meter 37° C. dialysis membrane (hemogas analyzer 1306) |
|---|---|---|
| a) HEPES/NaHEPES buffer | | |
| pH | 7.390 | 7.384 |
| | flame photom. | ISE |
| $Na^{+}$ | 146 | 140 |
| $K^{+}$ | 5.2 | 5.0 |
| | atomic. abs | |
| $Ca^{++}$ | 1.08 | 1.00 |
| b) MOPS/NaMOPS buffer | | |
| pH | 6.850 | 6.840 |
| | flame photom. | ISE |
| $Na^{+}$ | 101 | 100 |
| $K^{+}$ | 2.02 | 2.00 |
| | Ass. At | |

TABLE 10-continued

|  | pH meter 37° C. open liquid junction | pH meter 37° C. dialysis membrane (hemogas analyzer 1306) |
|---|---|---|
| $Ca^{++}$ | 3.06 | 3.00 |

The salts used for these standardization systems are stable, commercially obtainable and do not interfere with the determination at the electrodes. The phenylmercuric nitrate acts as a preservative and prevents any bacteria or mould growth in the proposed solutions without requiring sterilization, and does not interfere with or damage the electrodes for pH, sodium, potassium and calcium at the proposed concentrations.

The proposed standardization solutions reduce the error originating from the activity coefficient and from the presence of the liquid junction potential, to provide results for samples of normal blood (for total protein, cholesterol, triglyceride and plasma water contents), serum or plasma, which are in accordance with those determined for sodium and potassium by indirect methods (such as flame photometry or dil ISE) or by comparison methods for pH and ionized calcium conducted with existing commercial instrumentation.

The result of this invention is therefore to attain and offer a standardization system formulation which is suitable for and particularly dedicated to the simultaneous determination of pH and electrolytes in the blood, serum or plasma, with a chemical analyzer using ion-selective electrodes and which compares with instrumentation for the discrete determination of these quantities already described heretofore.

We claim:

1. A method for standardizing a clinical chemistry analyzer for the simultaneous determination by direct potentiometry of pH and concentrations of Na, K, Cl and Ca ions in blood, plasma or blood serum, comprising the steps of:
  a. providing ion selective electrodes specific for Na, K, Cl and Ca;
  b. contacting said electrodes with
    (i) a first buffer system comprising known concentrations of Na, K, Cl and Ca ions, a buffer pair comprising HEPES/NaHEPES N-2-hydroxyethylpiperazine-N-2-ethane sulphonic acid having a concentration of 40 to 60 mmol liter and a pH between 7.85 and 7.45; and
    (ii) a second buffer solution comprising known concentration of Na, K, Cl and Ca different from the first buffer solution, and a MOPS/NaMOPS 3-(N-morpholino)propane sulphonic acid buffer pair having a concentration of 40 to 60 mmol per liter and a pH between 6.80 and 6.90; and
  c. calibrating the clinical chemistry analyzer in accordance with the first and second buffer solutions.

2. The method of claim 1 wherein the concentration of the HEPES/NaHEPES buffer pair is 50 mmol/liter.

3. The method of claim 1 wherein the first buffer system comprises the following ions:

| Na | 146.5 mmol/liter |
|---|---|
| K | 5.2 mmol/liter |
| CA | 1.8 mmol/liter |
| Cl | 128.0 mmol/liter. |

4. The method of claim 3 wherein the first buffer system comprises:

| NaHEPES | 27.5 mmol/liter |
|---|---|
| HEPES | 22.36 mmol/liter |
| NaCl | 119.00 mmol/liter |
| $CaCl_2$ | 1.8 mmol/liter. |

5. The method of claim 1 wherein the concentration of the MOPS/NaMOPS buffer pair is 50 mmol/liter.

6. The method of claim 1 wherein the second buffer system comprises the following ions:

| Na | 101 mmol/liter |
|---|---|
| K | 2 mmol/liter |
| Ca | 3 mmol/liter |
| Cl | 23 mmol/liter. |

7. The method of claim 1 wherein the second buffer system comprises:

| NaMOPS | 23.25 mmol/liter |
|---|---|
| MOPS | 28.76 mmol/liter |
| NaCl | 77.75 mmol/liter |
| KCl | 2.02 mmol/liter |
| $CaCl_2$ | 3.06 mmol/liter. |

8. The method of claim 1 wherein the first and second buffer solutions further comprise 5 to 20 mg/liter of phenylmercuric nitrate.

9. A system for standardizing a clinical chemistry analyzer for the simultaneous determination by direct potentiometry of pH and concentration of Na, K, Cl and Ca ions in blood, plasma or blood serum, consisting essentially of:
  a first buffer system containing known concentrations of Na, K, Cl, and Ca ions, a HEPES/NaHEPES buffer pair having a concentration of between 40 to 60 mM and a pH between 7.35 to 7.45; and
  a second buffer system containing known concentrations of Na, K, Cl and Ca ions different from the first buffer solution, a MOPS/NaMOPS buffer pair having a concentration of 40 to 60 mmol per liter and a pH between 6.80 to 6.90.

10. The standardization system of claim 9 wherein the concentration of HEPES/NaHEPES is about 50 mmol/liter.

11. The standardization system of claim 10 wherein the first buffer solution contains the following ions in the following amounts:

| Na | 146.5 mmol/liter |
|---|---|
| K | 5.2 mmol/liter |
| Ca | 1.8 mmol/liter |
| Cl | 128.0 mmol/liter. |

12. The standardization system of claim 9 wherein the first buffer solution consists essentially of:

| NaHEPES | 27.5 mmol/liter |
|---|---|
| HEPES | 22.36 mmol/liter |
| NaCl | 119.0 mmol/liter |
| KCl | 5.2 mmol/liter |
| $CaCl_2$ | 1.8 mmol/liter. |

13. The standardization system of claim 9 wherein the concentration of MOS/NaMOPS is about 50 1 mmol/liter.

14. The standardization system of claim 13 wherein the second buffer solution contains the following ions in the following amounts:

| | |
|---|---|
| Na | 101.0 mmol/liter |
| K | 2.0 mmol/liter |
| Ca | 3.0 mmol/liter |

-continued

| | |
|---|---|
| Cl | 83.0 mmol/liter. |

15. The standardization system of claim 9 wherein the second buffer solution consists essentially of:

| | |
|---|---|
| NaMOPS | 23.25 mmol/liter |
| MOPS | 28.76 mmol/liter |
| NaCl | 77.75 mmol/liter |
| KCl | 2.02 mmol/liter |
| CaCl$_2$ | 3.06 mmol/liter. |

* * * * *